US 8,401,246 B2

(12) United States Patent
Huang et al.

(10) Patent No.: US 8,401,246 B2
(45) Date of Patent: Mar. 19, 2013

(54) MAPPING OF RETINAL PARAMETERS FROM COMBINED FUNDUS IMAGE AND THREE-DIMENSIONAL OPTICAL COHERENCE TOMOGRAPHY

(75) Inventors: Yijun Huang, Pleasantville, NY (US); Tetsuyoshi Royama, Montvale, NJ (US); Alexandre Kotchkin, Ridgewood, NJ (US)

(73) Assignee: Topcon Medical Systems, Inc., Oakland, NJ (US)

( * ) Notice: Subject to any disclaimer, the term of this patent is extended or adjusted under 35 U.S.C. 154(b) by 1147 days.

(21) Appl. No.: 12/262,799

(22) Filed: Oct. 31, 2008

(65) Prior Publication Data

US 2009/0123036 A1 May 14, 2009

Related U.S. Application Data

(60) Provisional application No. 61/002,363, filed on Nov. 8, 2007.

(51) Int. Cl.
G06K 9/00 (2006.01)
(52) U.S. Cl. ........ 382/117; 351/206; 351/210; 382/128; 382/154; 382/284
(58) Field of Classification Search .................. 351/206, 351/210; 382/106, 117, 284
See application file for complete search history.

(56) References Cited

U.S. PATENT DOCUMENTS

| | | | | |
|---|---|---|---|---|
| 7,341,347 B2* | 3/2008 | Pearson et al. | ................ | 351/206 |
| 7,505,142 B2* | 3/2009 | Knighton et al. | ............ | 356/479 |
| 7,593,559 B2* | 9/2009 | Toth et al. | ..................... | 382/128 |
| 7,641,338 B2* | 1/2010 | Fukuma et al. | ............... | 351/206 |
| 7,641,339 B2* | 1/2010 | Hangai et al. | ................ | 351/206 |
| 7,668,342 B2* | 2/2010 | Everett et al. | ................ | 382/106 |
| 7,784,942 B2* | 8/2010 | Maeda et al. | ................ | 351/206 |
| 7,813,589 B2* | 10/2010 | Silverstein et al. | ........... | 382/284 |
| 7,905,597 B2* | 3/2011 | Tsukada et al. | ............... | 351/206 |
| 8,134,554 B1* | 3/2012 | Huang et al. | .................. | 345/424 |
| 8,223,143 B2* | 7/2012 | Dastmalchi et al. | .......... | 345/418 |
| 2005/0094099 A1 | 5/2005 | Newman et al. | | |
| 2007/0115481 A1* | 5/2007 | Toth et al. | ..................... | 356/511 |
| 2007/0216909 A1 | 9/2007 | Everett et al. | | |
| 2009/0123036 A1* | 5/2009 | Huang et al. | .................. | 382/117 |
| 2010/0142780 A1* | 6/2010 | Yasuno et al. | ................ | 382/131 |

OTHER PUBLICATIONS

PCT International Search Report corresponding to PCT Patent Application PCT/US2008/012507 filed Nov. 6, 2008 (3 pages).
PCT Written Opinion of the International Searching Authority corresponding to PCT Patent Application PCT/US2008/012507 filed Nov. 6, 2008 (5 pages).
U.S. Appl. No. 11/800,186, filed May 4, 2007.
B. Cense, et. al. "Thickness and Birefringence of Healthy Retinal Nerve Fiber Layer Tissue Measured with Polarization-Sensitive Optical Coherence Tomography." Investigative Ophthalmology & Visual Science, Aug. 2004, vol. 45, No. 8, pp. 2606-2612.

(Continued)

*Primary Examiner* — Gregory M Desire
(74) *Attorney, Agent, or Firm* — Wolff & Samson PC

(57) ABSTRACT

A second retinal characterization data set is mapped to a first retinal characterization dataset. The first retinal characterization dataset is displayed as a first graphical map. The second retinal characterization dataset is displayed as a second graphical map which is mapped to the first graphical map. The second graphical map may be warped and morphed onto the first graphical map. Retinal characterization datasets may be derived either from a fundus image or from a retinal parameter dataset calculated from a three-dimensional optical coherence tomography scan of a retina. Retinal parameter datasets may characterize parameters such as retinal thickness. In an embodiment, a fundus image is warped and morphed onto a retinal surface topographical map.

30 Claims, 11 Drawing Sheets

OTHER PUBLICATIONS

M. Gabriele, et al. "Peripapillary Nerve Fiber Layer Thickness Profile Determined with High Speed, Ultrahigh Resolution Optical Coherence Tomography High-Density Scanning." Investigative Ophthalmology & Visual Science, Jul. 2007, vol. 48, No. 7, pp. 3154-3160.

G. Garcia-Sanchez, et. al. "Measurement of retinal nerve fiber layer thickness in normal and glaucomatous Cocker Spaniels by scanning laser polarimetry." Veterinary Ophthalmology (2007) 10, Supplement 1, pp. 78-87.

D. Garway-Heath, et al. "Mapping the Visual Field to the Optic Disc in Normal Tension Glaucoma Eyes." Ophthalmology 2000; 107: pp. 1809-1815.

H. Ishikawa, et. al. "Retinal Nerve Fiber Layer Assessment Using Optical Coherence Tomography with Active Optic Nerve Head Tracking." Investigative Ophthalmology & Visual Science, Mar. 2006, vol. 47, No. 3, pp. 964-967.

Carl Zeiss Meditec Inc. "Stratus OCT Real Answers in Real Time." 2005.

M. Sandberg, et al., "The Association Between Visual Acuity and Central Retinal Thickness in Retinitis Pigmentosa", Investigative Ophthalmology & Visual Science, Sep. 2005, vol. 46, No. 9, pp. 3349-3354.

A. Neubrauer, et al., "Tele-Screening for Diabetic Retinopathy with the Retinal Thickness Analyzer", Diabetes Care, vol. 26, No. 10, Oct. 2003, pp. 2890-2897.

W. Goebel, et al., "Retinal Thickness in Diabetic Retinopathy", Retina, The Journal of Retinal and Vitreous Diseases, 2006, vol. 26, No. 1, pp. 49-57.

P. Fritsche, et al., "Retinal Thickness Analysis (RTA)", Retina, The Journal of Retinal and Vitreous Diseases, 2002, vol. 22, No. 6, pp. 768-771.

\* cited by examiner

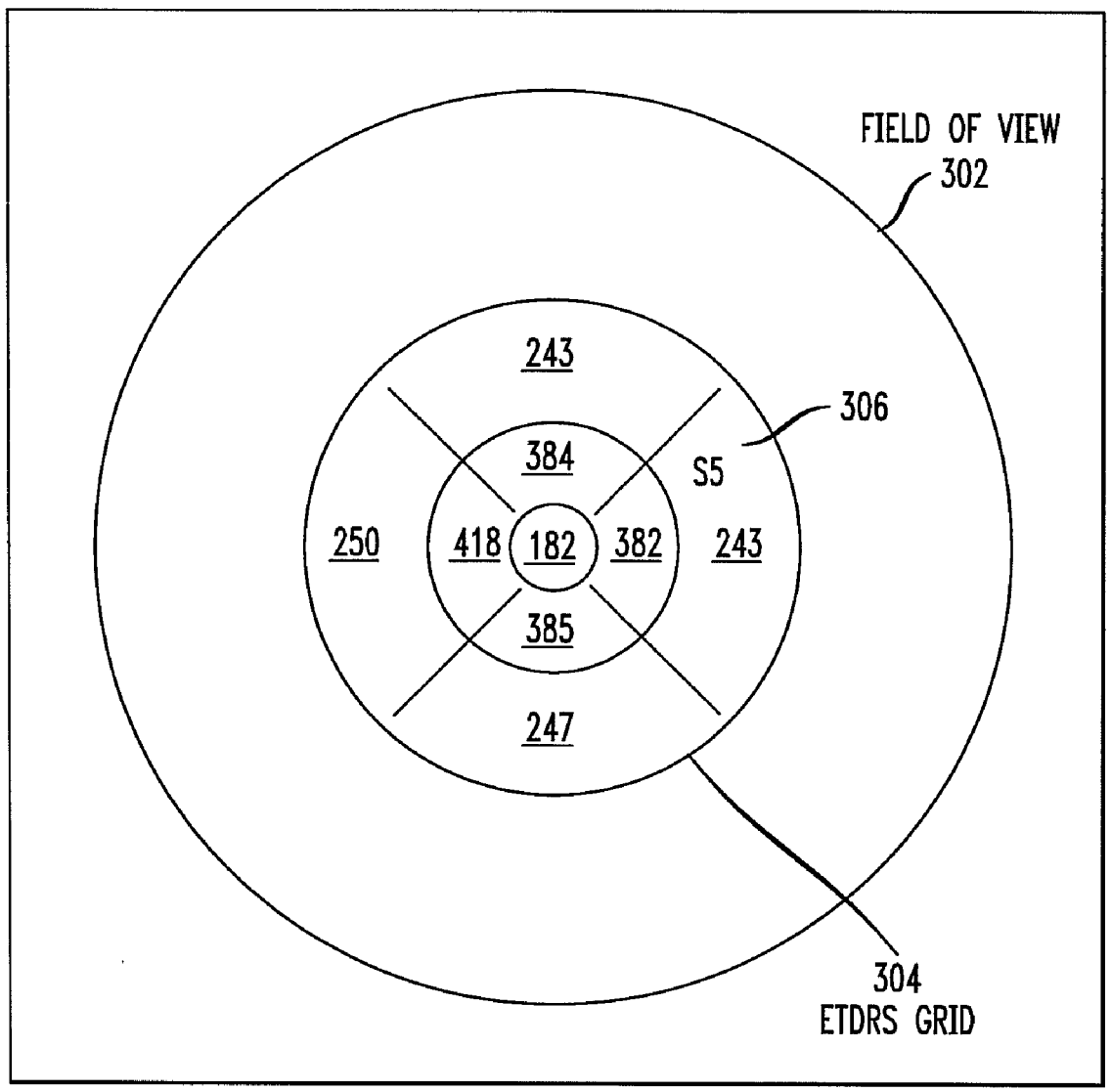

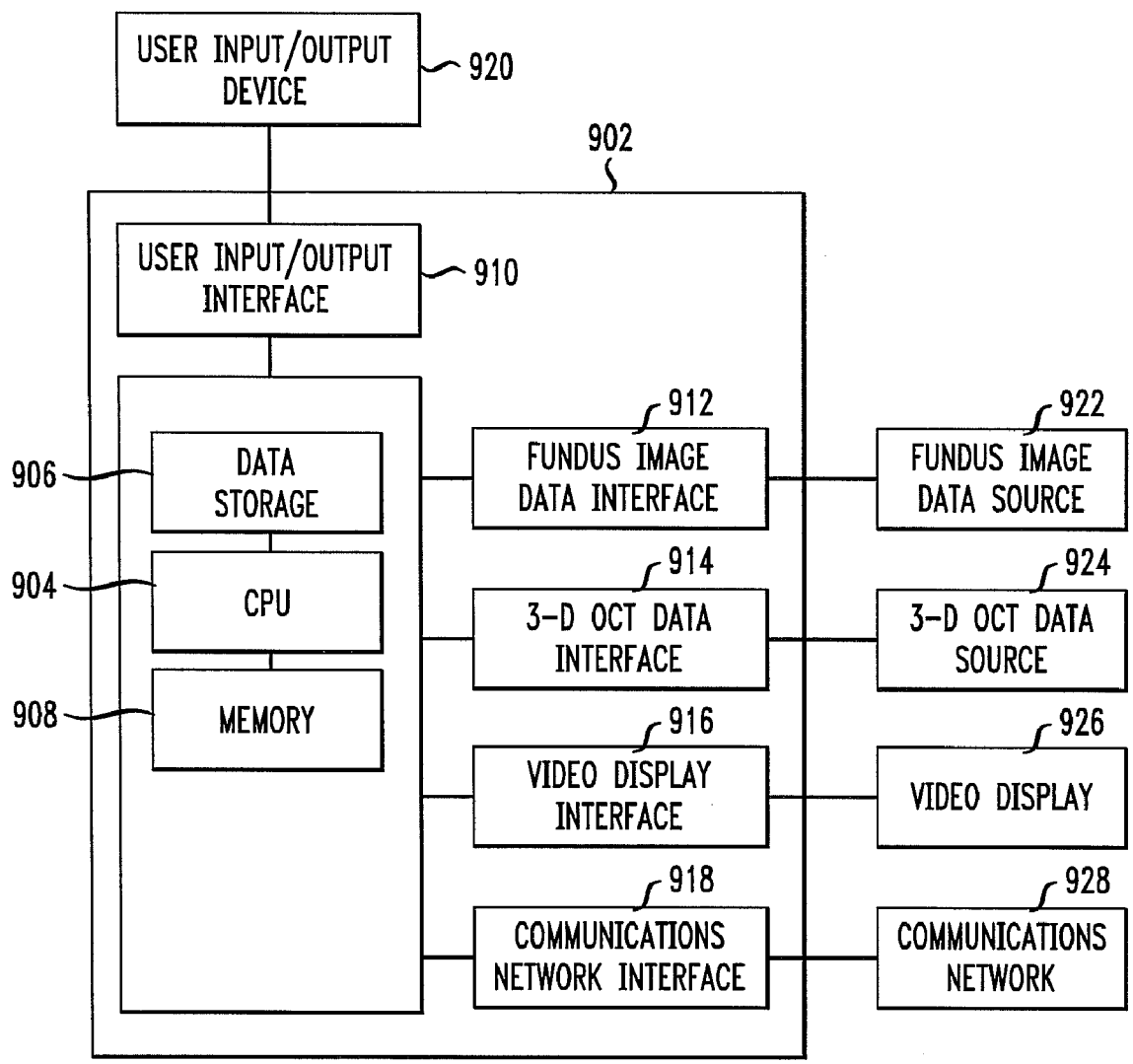

MAPPING OF RETINAL PARAMETERS FROM COMBINED FUNDUS IMAGE AND THREE-DIMENSIONAL OPTICAL COHERENCE TOMOGRAPHY

This application claims the benefit of U.S. Provisional Application No. 61/002,363 filed Nov. 8, 2007, which is incorporated herein by reference.

BACKGROUND OF THE INVENTION

The present invention relates generally to ophthalmic characterization, and more particularly to mapping retinal parameters from combined fundus image and three-dimensional optical coherence tomography.

Diagnostics for eye disorders typically include a detailed ophthalmic examination of the retina. For initial examination, an eye doctor will view the retina through an ophthalmoscope. For a permanent record, the retina is typically photographed with a fundus camera. A fundus photograph directly records various anatomical features of the retina, such as the optic disc, fovea, blood vessels, and lesions. The imaging capabilities of fundus photography may be enhanced by supplementary techniques. A high-contrast image of retinal blood vessels, for example, may be photographed after the injection of a fluorescent dye into the bloodstream. The resulting image is referred to as a fluorescein angiogram (FA).

More sophisticated techniques have recently been developed for diagnostics of the eye. One such technique is three-dimensional optical coherence tomography (3-D OCT). In this technique, a light beam is directed onto the retina. Part of the beam is back-reflected. Interferometric analysis of the back-reflected light yields information on the structure of the retina. By varying optical parameters of the light probe, features at different depths below the surface of the retina may be probed. With this process, an image of a cross-section of the retina may be generated by scanning the optical probe along a line on the retina. By rastering the optical probe across the surface of the retina, a series of cross-sectional images may be produced. The series of cross-sectional images may be used to characterize the 3-D structure of the retina, and parameters such as local retinal thickness may be measured by 3-D OCT.

The retinal thickness is dependent on the loci (points on the retina) at which the measurements are made. Of particular interest for diagnostics of the eye are variations of retinal thickness in a region about an anatomical feature. Some analytical instruments may provide a table of numerical values of retinal thickness as a function of position (specified by coordinates) on a retina. Other analytical instruments may map numerical values of retinal thickness to a grid covering the field of the retinal plane. Correlating numerical values of retinal thickness, either in tabular or grid format, with anatomical features is a difficult and, at best, a static process. What are needed are method and apparatus for a user, such as an ophthalmologist, to view a graphical representation of retinal thickness, or other parameter characterizing the retina, simultaneously with an image of anatomical structures in the retina. Method and apparatus which allow a user to view a graphical representation of a first parameter characterizing the retina mapped to a second parameter characterizing the retina are further advantageous.

BRIEF SUMMARY OF THE INVENTION

A second retinal characterization data set is mapped to a first retinal characterization dataset. The first retinal characterization dataset is displayed as a first graphical map. The second retinal characterization dataset is displayed as a second graphical map which is mapped to the first graphical map. The second graphical map may be warped and morphed onto the first graphical map. Retinal characterization datasets may be derived either from a fundus image or from a retinal parameter dataset calculated from a three-dimensional optical coherence tomography scan of a retina. Retinal parameter datasets may characterize parameters such as retinal thickness.

These and other advantages of the invention will be apparent to those of ordinary skill in the art by reference to the following detailed description and the accompanying drawings.

BRIEF DESCRIPTION OF THE DRAWINGS

FIG. 3 shows average retinal thickness values displayed on an ETDRS grid;

FIG. 9 shows a schematic of a measurement and image processing system implemented with a computer.

DETAILED DESCRIPTION

Diagnostics for eye disorders typically include a detailed ophthalmic examination of the retina. For initial examination, an eye doctor will view the retina through an ophthalmoscope. For a permanent record, the retina is typically photographed with a fundus camera. A fundus photograph directly records various anatomical features of the retina, such as the optic disc, fovea, blood vessels, and lesions. The image may be captured on film or stored in digital form and displayed on a monitor. Visual inspection of the retina continues to be a primary diagnostic technique.

More sophisticated techniques have recently been developed for diagnostics of the eye. A powerful technique for characterizing and imaging ocular structures, including the retina, is three-dimensional optical coherence tomography (3-D OCT). In this technique, an optical probe, typically a laser beam, is directed onto the retina. Part of the beam is back-reflected. Interferometric analysis of the back-reflected light yields information on the structure of the retina. By varying optical parameters of the optical probe, features at different depths below the surface of the retina may be probed. With this process, an image of a cross-section of the retina may be generated by scanning the optical probe along a line on the retina. By rastering the optical probe across the surface of the retina, a series of cross-sectional images may be produced. The series of cross-sectional images characterize the 3-D structure of the retina, and parameters such as local retinal thickness may be measured by 3-D OCT.

Figure 1B:
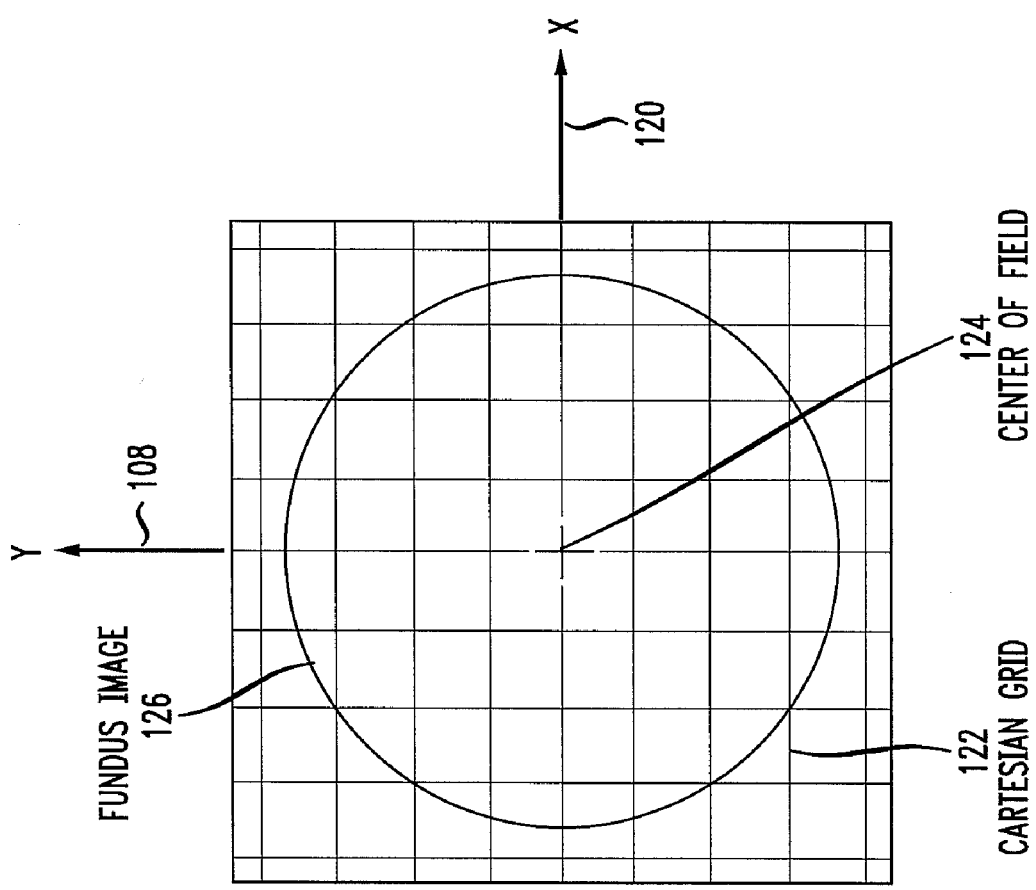
FIG. 1(a) and FIG. 1(b) show a Cartesian coordinate system for a retina.
Figure 1A:
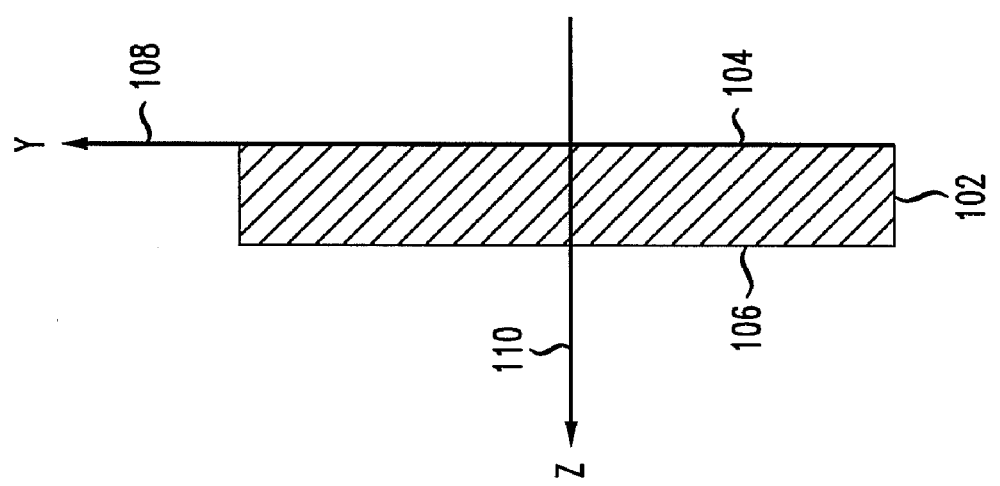

FIG. 1(a) and FIG. 1(b) show a reference coordinate system for a retina. FIG. 1(a) is a cross-sectional view, and FIG. 1(b) is a frontal view. Although a retina is a curved structure, it may be approximated by a planar structure, as represented in FIG. 1(a) by cross-section plane 102 with front surface plane 104 and rear surface plane 106. The front surface plane 104, for example, may be that which is viewed by an observer through an ophthalmoscope or photographed by a fundus camera. In a standard Cartesian coordinate system, the cross-section plane 102, as shown in FIG. 1(a), is the Y-Z plane, indicated by Y-axis 108 and Z-axis 110. The positive direction of Z runs from the front surface plane 104 to the rear surface plane 106, with Z=0 defined at the front surface plane 104. The Z-coordinate indicates the depth of a layer below the front surface plane 104. In some applications, the origin Z=0 is in front of the retinal plane, such that the Z coordinate of the front surface plane 104 of the retina is an offset value $\Delta Z$. Strictly, then, the Z-coordinate $Z_D$ of a point at a depth D below the surface of the retina is $Z_D = D + \Delta Z$ To simplify the discussions below, $\Delta Z$ is set to 0, unless otherwise stated.

The front surface plane 104 in FIG. 1(a), viewed along the +Z direction, is represented in FIG. 1(b) by the X-Y plane, indicated by X-axis 120 and Y-axis 108. Herein, the X-Y plane is also referred to as the retinal plane. The circle denoted Fundus Image 126 is a schematic representation of the field of a fundus image (no features are shown in this example). The origin of the Cartesian Grid 122 may be specified by a user, such as an ophthalmologist. In FIG. 1(b), the origin is placed at the center of Fundus Image 126, denoted Center of Field 124.

A 3-D OCT scan measures back-reflected optical signal intensities from a 3-D matrix of discrete points in a retina. In a one-dimensional OCT-A scan, the signal intensity is measured as a function of depth. The optical probe is held fixed at a constant lateral position (for example, $X=X_1, Y=Y_1$) on the retinal plane, and the signal intensity is measured at a set of discrete points with values of Z ranging from $Z_{min}$ to $Z_{max}$. A set of OCT-A scans is then taken along a line. For example, $Y=Y_1$ is held fixed, while OCT-A scans are taken at a discrete set of points with values of X ranging from $X_{min}$ to $X_{max}$. This set of OCT-A scans, referred to as an OCT-B scan, yields the signal intensities from a two-dimensional (2-D) matrix of points lying in a cross-sectional plane perpendicular to the retinal plane. A set of OCT-B scans is then taken over a region of the retina. For example, OCT-B scans are taken at a discrete set of points with values of Y ranging from $Y_{min}$ to $Y_{max}$.

Herein, a 3-D OCT volume dataset refers to a set of back-reflected optical signal intensities acquired from a 3-D matrix of discrete points in a retina. A 3-D graphical representation of a 3-D OCT volume dataset comprises a 3-D matrix of voxels, wherein a voxel corresponds to a graphical element at a discrete point in the retina. A 3-D volume dataset acquired from 3-D OCT scans may be rendered to display images on a 2-D display, such as a computer monitor. The 3-D volume dataset, for example, may be mapped to luminance values of pixels for monochrome displays and luminance and false color values of pixels for color displays. Various images may be rendered from the 3-D volume dataset, for example, 2-D cross-sectional images, 2-D composite images, and 3-D perspective images. Herein, a 2-D composite image refers to a 2-D image rendered from a 3-D volume dataset and displayed on a user-defined plane. One skilled in the art may develop embodiments which apply to 3-D volume datasets acquired from other modalities.

Figure 2:
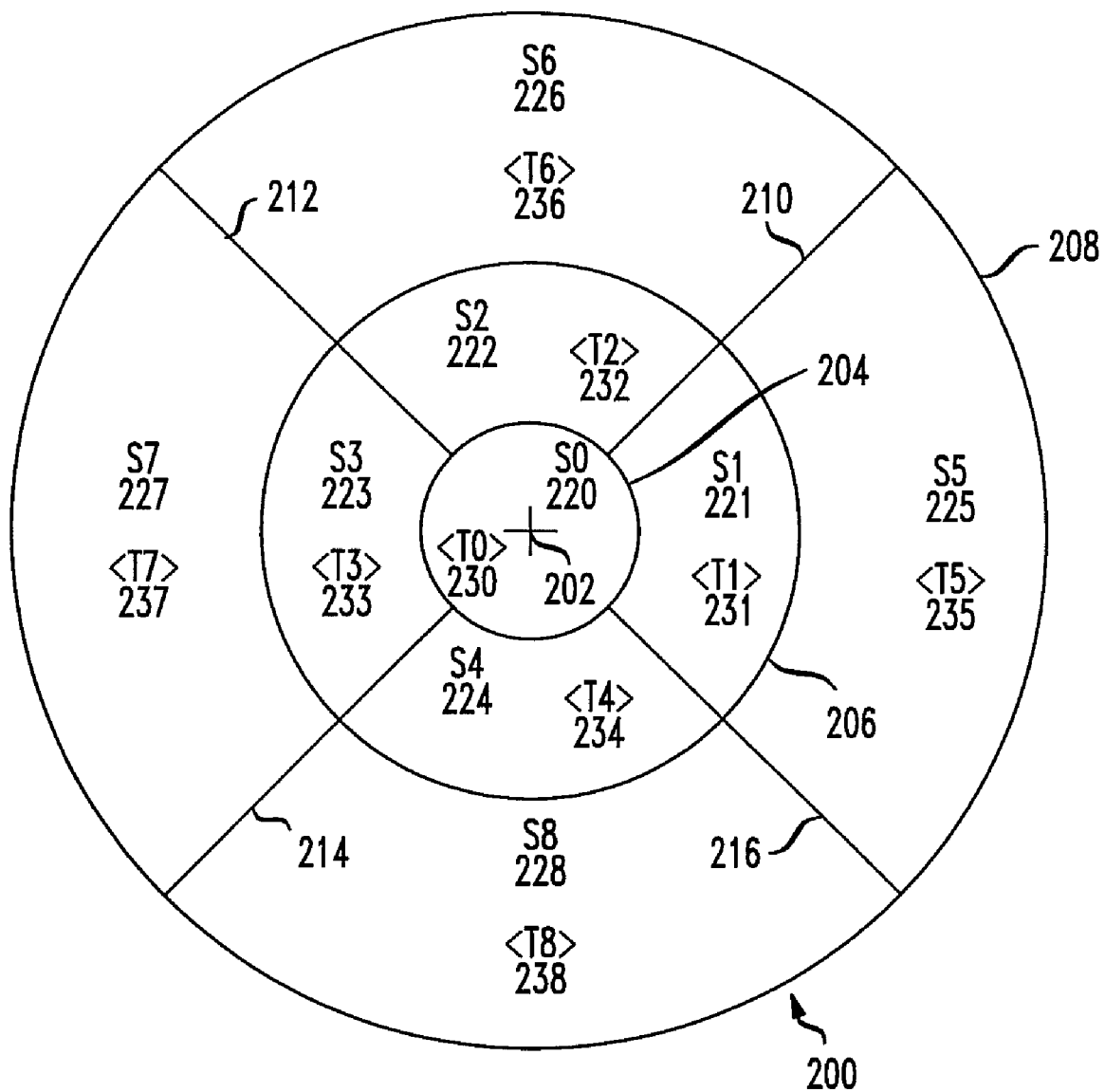
FIG. 2 shows a generic Early Treatment Diabetic Retinopathy Study (ETDRS) grid.

Some analytical instruments measure retinal thickness at a fixed set of measurement loci on the retina. The data is presented in tabular form, or displayed on a measurement grid. No fundus image is presented. The Early Treatment Diabetic Retinopathy Study (ETDRS) grid, commonly used in ophthalmology, is shown in FIG. 2. The ETDRS Grid 200 comprises three concentric circles, Circle 204-Circle 208, centered at Center 202. Four radial lines, Radial Line 210-Radial Line 216, partition the measurement field into a measurement grid with nine sectors, labelled S0 220-S8 228. Sector S0 220 is the entire inner circular region contained within Circle 204. The other sectors, S1 221-S8 228, are portions (wedges) of annular rings. The center of the grid, Center 202, is referenced, for example, to the center of the fovea.

Retinal thicknesses within a sector may be characterized by statistical values, herein referred to as summary values, such as average, median, minimum, maximum, standard deviation, quartile, interquartile range, interquartile mean, quantile, or percentile values. A summary value characterizing the retinal thickness within a sector is denoted herein as <T>. Herein, a summary value characterizing the retinal thickness within a sector is mapped to the sector. Herein, a set of summary values characterizing the retinal thickness over the region of the measurement grid is mapped to the measurement grid. In FIG. 2, for example, values <T0> 230-<T8> 238 are mapped to sectors S0 220-S8 228, respectively.

FIG. 3 shows a typical readout. The Field of View 302 represents the region of the retina visible during measurement. Note that Field of View 302 does not represent a fundus image. The numbers displayed within the sectors of ETDRS Grid 304 are the average values of retinal thickness within each sector. For example, the average retinal thickness in sector S5 306 of ETDRS GRID 304 is 243 microns.

With 3-D OCT, measurements are not limited to a fixed set of loci. Processing of the data permits analysis at the full set of discrete points within the 3-D OCT volume dataset. As discussed above, anatomical features are typically photographed by a fundus camera. The image may be stored in digital form and displayed on a monitor. In an embodiment, a 3-D OCT volume dataset is registered to a fundus image by registering a 2-D composite image (rendered from the 3-D OCT volume dataset) to the fundus image. Once the 3-D OCT volume dataset has been registered to the fundus image, retinal thickness measurements may be mapped to loci referenced to specific anatomical features. One skilled in the art may develop embodiments in which the 3-D OCT volume dataset is registered to a 2-D image produced by other modalities.

Figure 4A:
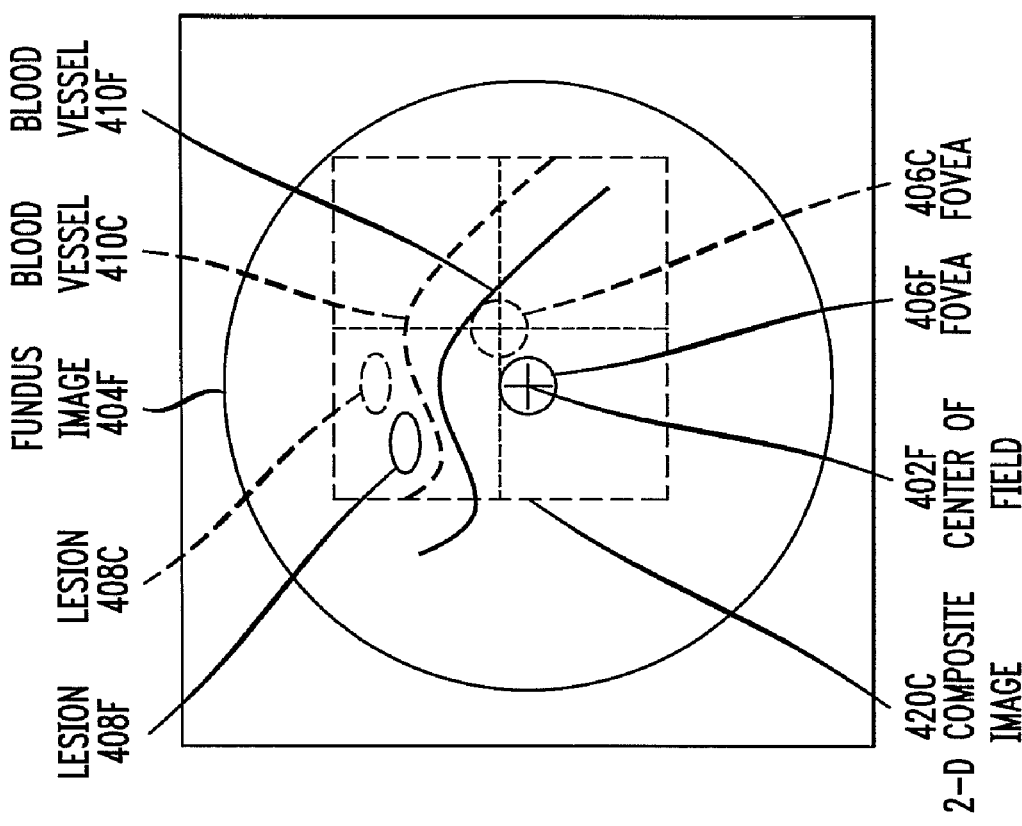
FIG. 4(a) shows schematic representations of characteristic features on a fundus image.
Figure 4B:
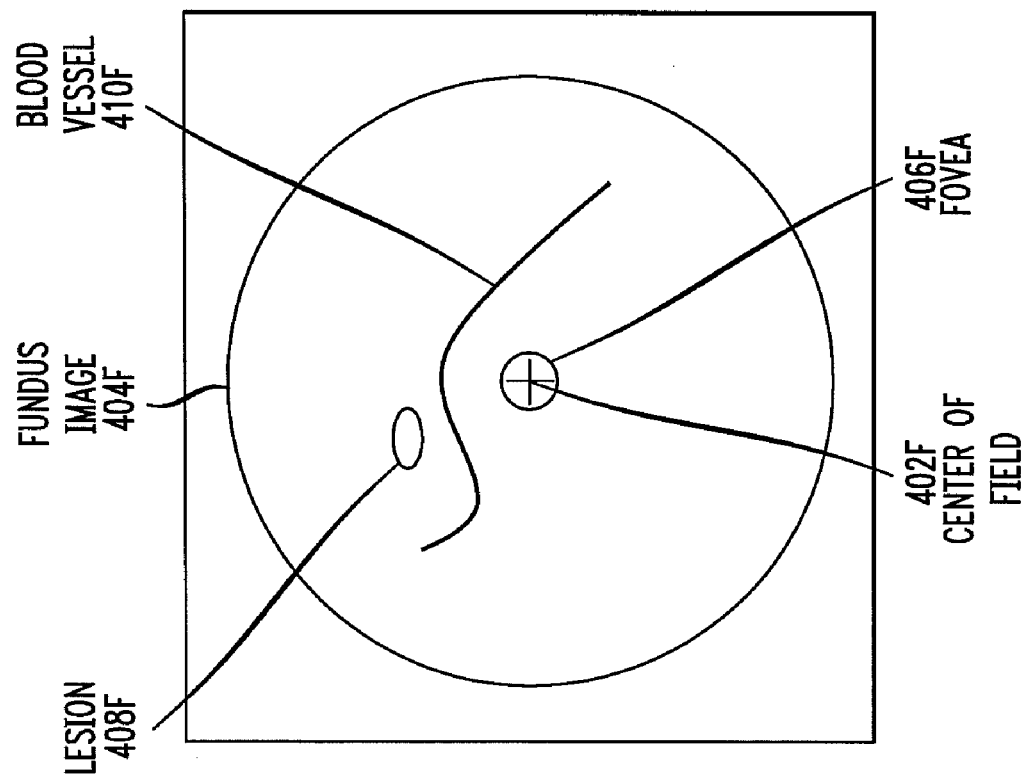
FIG. 4(b) shows schematic representations of corresponding characteristic features in a fundus image and in a two-dimensional composite image.

FIG. 4(a) and FIG. 4(b) illustrate an embodiment, as described in U.S. patent application Ser. No. 11/800,186, for registering a 3-D OCT volume dataset with a fundus image. In FIG. 4(a), the fundus image is schematically represented by Fundus Image 404F, centered at Center of Field 402F. Graphical representations of characteristic features, such as Fovea 406F, Lesion 408F, and Blood Vessel 410F, are shown. To simplify the terminology, herein, a "graphical representation of a characteristic feature" is also referred to simply as the "characteristic feature". Characteristic features are also referred to herein as landmarks or spatial indicia.

In FIG. 4(b), the dashed square, denoted 2-D Composite Image 420C, represents the field of a 2-D composite image rendered from a 3-D OCT volume dataset. In an embodiment, a 2-D composite image provides a frontal view, that is, a view corresponding to the fundus image. The 3-D OCT volume dataset may be registered to the fundus image by scaling, orienting, and aligning characteristic features in the 2-D composite image with the corresponding characteristic features in the fundus image. In FIG. 4(b), for example, characteristic features Fovea 406C, Lesion 408C, and Blood Vessel 410C in the 2-D Composite Image 420C correspond to characteristic features Fovea 406F, Lesion 408F, and Blood Vessel 410F in Fundus Image 404F. In this example, 2-D Composite Image 420C has already been processed to have the same scale and orientation as Fundus Image 404F; however, there is a uniform translation between the two images.

Herein, a characteristic feature in a first image corresponds to a characteristic feature in a second image, if the characteristic feature in the first image and the characteristic feature in the second image are the same. Herein, if a characteristic feature in the first image corresponds to a characteristic feature in the second image, then the characteristic feature in the second image also corresponds to the characteristic feature in the first image. Herein, a first image and a second image may be produced by different modalities (such as a fundus image and a 2-D composite image rendered from a 3-D OCT volume dataset) or by the same modality at different times. One skilled in the art may develop embodiments using modalities other than a fundus image or a 2-D composite image.

Figure 4C:
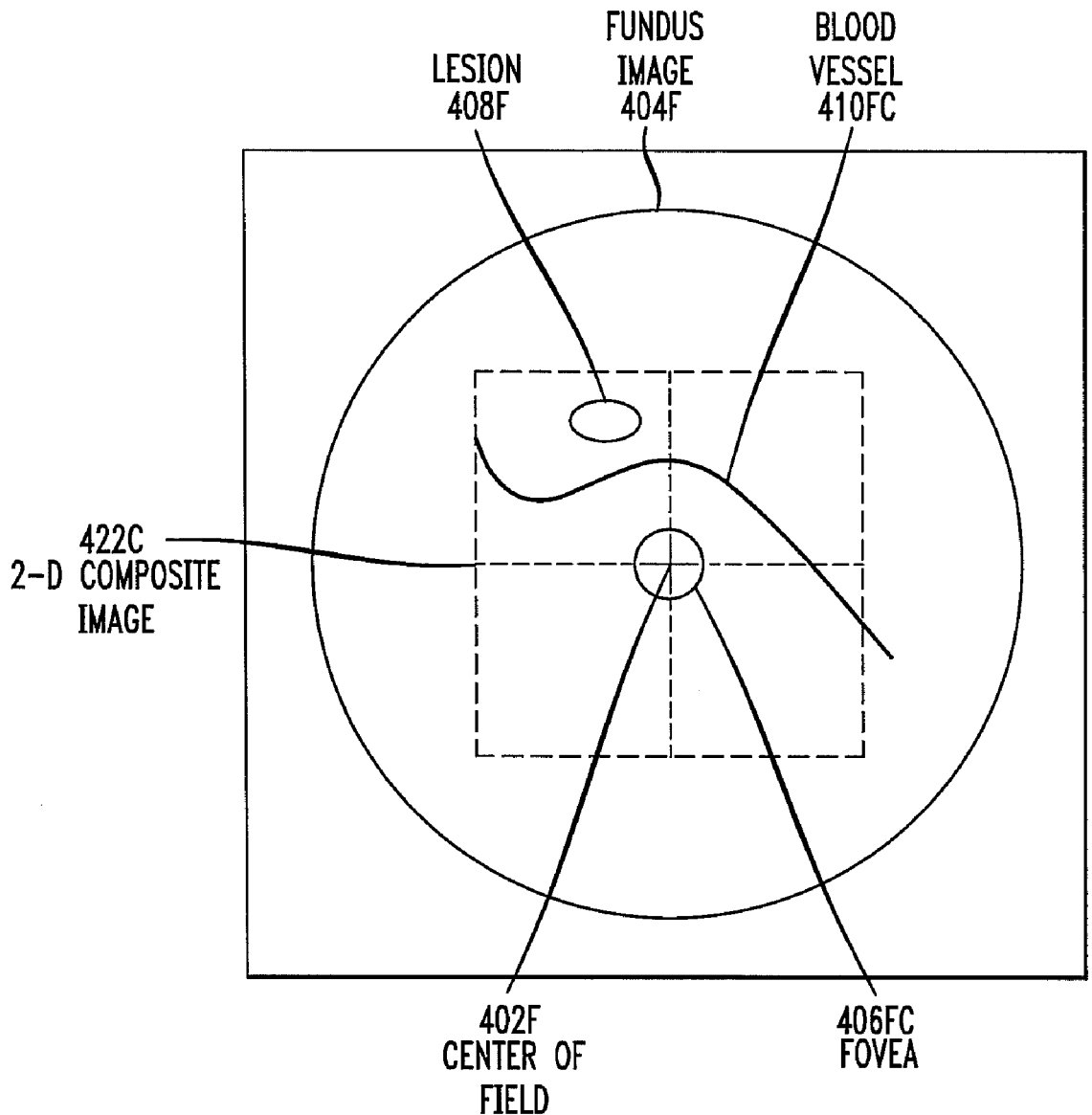
FIG. 4(c) shows a two-dimensional composite image superimposed onto a fundus image.
Figure 4D:
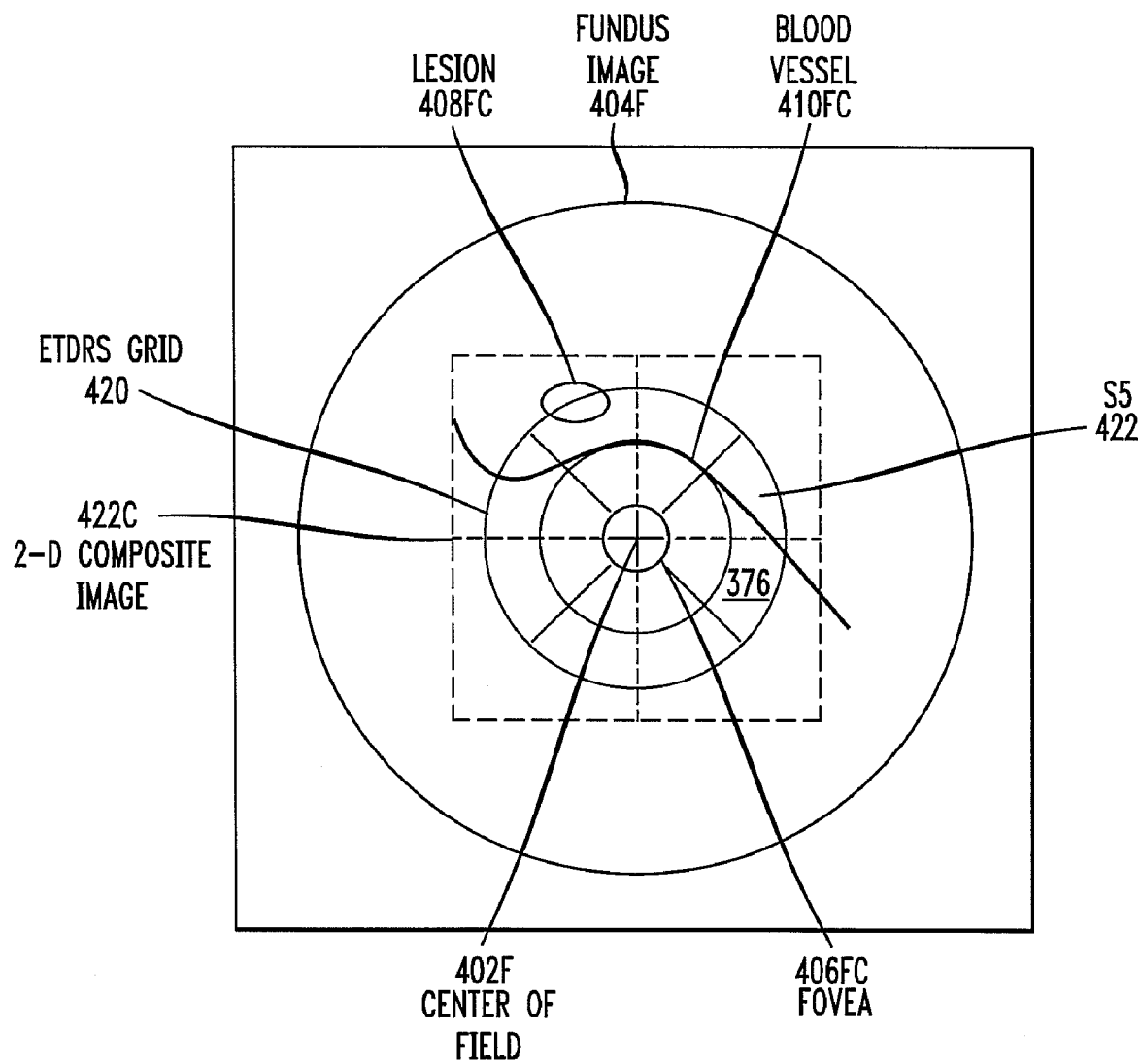
FIG. 4(d) shows an ETDRS grid superimposed onto a combined fundus image and two-dimensional composite image.

In an embodiment, Fundus Image 404F and 2-D Composite Image 420C are displayed on a monitor. The Fundus Image 404F remains fixed in the field of view, while the 2-D Composite Image 420C may be freely moved. For example, a user may use a mouse to position a cursor on 2-D Composite Image 420C, click on it, and drag it over Fundus Image 404F until characteristic features Fovea 406C, Lesion 408C, and Blood Vessel 410C in the 2-D Composite Image 420C are superimposed onto the corresponding characteristic features Fovea 406F, Lesion 408F, and Blood Vessel 410F in Fundus Image 404F. The results are shown in FIG. 4(c), in which the characteristic features in the superimposed images are denoted Fovea 406FC, Lesion 408FC, and Blood Vessel 410FC. In an embodiment, the user may also change the scale and orientation of 2-D Composite Image 420C. In an embodiment, superposition of characteristic features in 2-D Composite Image 420C onto corresponding characteristic features in Fundus Image 404F may be performed with automatic image recognition and processing. Note that superposition of multiple corresponding characteristic features provides more precise registration than superposition of a single characteristic feature, such as the fovea. Since, in general, characteristic features may have irregular shapes, and their boundaries may not be distinct, the precision of registration improves as the number of corresponding characteristic features increases.

Figure 5:
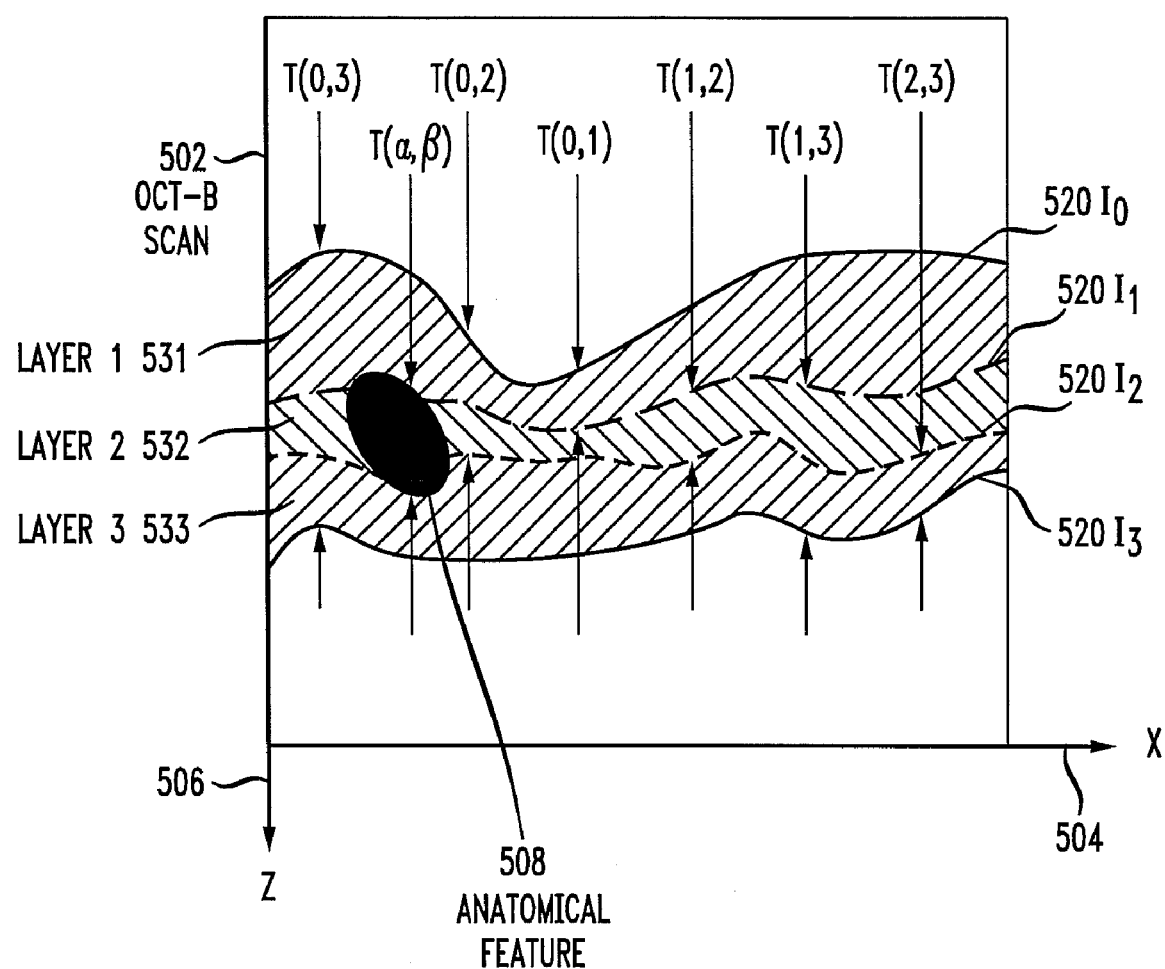
FIG. 5 shows a schematic representation of an OCT-B scan.

In an embodiment, retinal thickness is mapped to a surface topographical map of the retinal surface. FIG. 5 shows a schematic of an OCT-B Scan, denoted OCT-B Scan 502, displaying a cross-section perpendicular to the retinal plane (see FIG. 1(a) and FIG. 1(b)). The plane of the OCT-B Scan 502 is the X-Z plane (at a constant value of Y), indicated by X-Axis 504 and Z-Axis 506. Three layers, delineated by four interfaces, denoted $I_0$ 520-$I_3$ 523, are visible. Shown also is an anatomical feature, denoted Anatomical Feature 508, such as a lesion.

The outer surface of the retina is delineated by interface $I_0$ 520, and the inner surface of the retina is delineated by interface $I_3$ 523. The interfaces $I_1$ 521 and $I_2$ 522 delineate interior layers. The outermost layer, Layer1 531, is the region bounded by $I_0$ 520 and $I_1$ 521. The middle layer, Layer2 532, is the region bounded by $I_1$ 521 and $I_2$ 522. The innermost layer, Layer3 533, is the region bounded by $I_2$ 522 and $I_3$ 523. From the OCT-B Scan 502, the thickness of a layer, or a combination of layers, may be measured. These are shown as T(0,3), T(0,2), T(0,1), T(1,2), T(1,3), and T(2,3). An arbitrary thickness $T(\alpha,\beta)$ at a feature of interest, such as Anatomical Feature 508, may also be measured. As shown in FIG. 5, the thickness of each layer may vary as a function of X. By generating OCT-B scans at different values of Y, retinal layer thickness may be mapped across the surface of the retina.

Figure 6A:
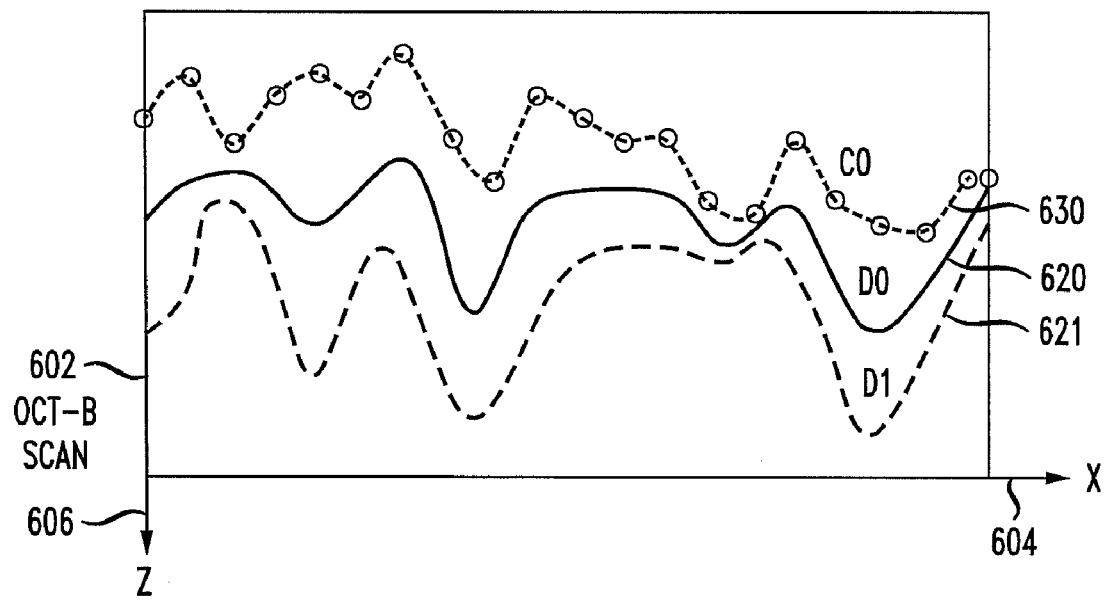
FIG. 6(a) shows a graphical representation of values of retinal thickness mapped to a retinal surface profile.
Figure 6B:
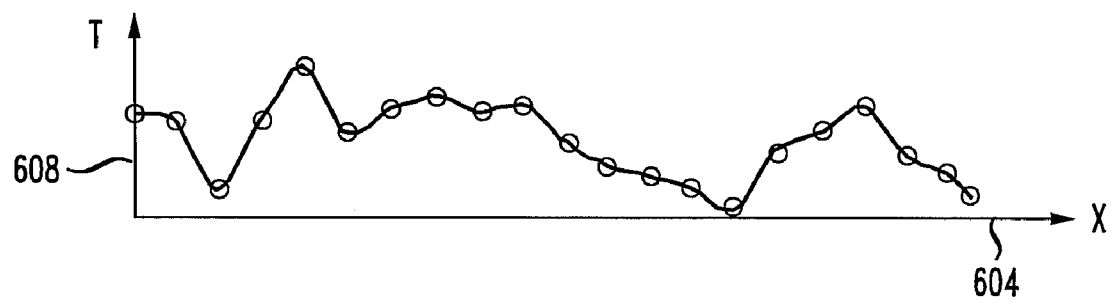
FIG. 6(b) shows a plot of retinal thickness as a function of position.

An embodiment for mapping retinal layer thickness onto the surface profile of the retina is shown in FIG. 6(a) and FIG. 6(b). FIG. 6(a) shows a schematic of an OCT-B Scan, denoted OCT-B Scan 602, displaying a cross-section perpendicular to the retinal plane (see FIG. 1(a) and FIG. 1(b)). The plane of the OCT-B Scan 602 is the X-Z plane (at a constant value of Y), indicated by X-Axis 604 and Z-Axis 606. For simplicity, only one layer is shown, delineated by interface D0 620 and D1 621. In this example, interface D0 620 represents the outer surface profile of the retina.

In this example, the profile of interface D0 620 is defined by the function:

$$Z = D_0(X) \qquad \text{Eqn. 1}$$

Similarly, the profile of interface D1 621 is defined by the function:

$$Z = D_1(X) \qquad \text{Eqn. 2}$$

Here, Y is held constant. In this example, the origin Z=0 is displaced in front of the nominal retinal plane, since the surface of the retina is not truly planar. The thickness of the retinal layer bounded by D0 620 and D1 621 is $$T(X) = D_1(X) - D_0(X) \qquad \text{Eqn. 3}$$

In FIG. 6B, the thickness T(X) is plotted as a function of X. The vertical axis is denoted T 608. The profile C0 630 in FIG. 6(a) is generated by the function:

$$C_0(X) = D_0(X) - T(X) \qquad \text{Eqn. 4}$$

$$C_0(X) = 2D_0(X) - D_1(X) \qquad \text{Eqn. 5}$$

The profile C0 630 maps the retinal layer thickness to the outer surface profile D0 620 of the retina. In the example shown in FIG. 6(a), the profile C0 630 is superimposed onto OCT-B Scan 602. Profile C0 630 may also be displayed separately, either by itself, in combination with other profiles, or in combination with a fundus image. FIG. 6(a) shows an example in two dimensions. In a 3-D graphical representation, the outer surface of the retina may be represented by a surface topographical map defined by the function $Z=\sigma(X, Y)$. In an embodiment, a map representing retinal layer thickness defined by the function $Z=\tau(X,Y)$ is mapped to the surface topographical map to generate a composite map. A more detailed discussion of a composite map is given below. Various image processing techniques, such as warping and morphing, may be used to generate the composite map.

In an embodiment, a set of values of a second retinal parameter is mapped to a set of values of a first retinal parameter. Herein, a retinal parameter refers to any parameter which characterizes a property of the retina. Examples of retinal parameters include thickness, volume, density, diameters of anatomical features, and the number of anatomical features per unit area. Herein, a value of a retinal parameter may refer either to the value of a retinal parameter at a point in the retina or to a summary value of the retinal parameter in a neighborhood around a point in the retina. As discussed above, a summary value refers to a statistical value which characterizes the values of the retinal parameter within the neighborhood. Note that the shape, size, and configuration of a neighborhood do not need to be uniform. Neighborhoods do not need to be contiguous.

Herein, a set of values of a retinal parameter is also referred to as a retinal parameter dataset. Note that a first retinal parameter dataset and a second retinal parameter dataset may refer to two separate physical parameters in the same retina, or to the same physical parameter in the same retina at different times. A first retinal parameter dataset and a second retinal parameter dataset may also refer to retinal parameters in different retinas.

Figure 7A:
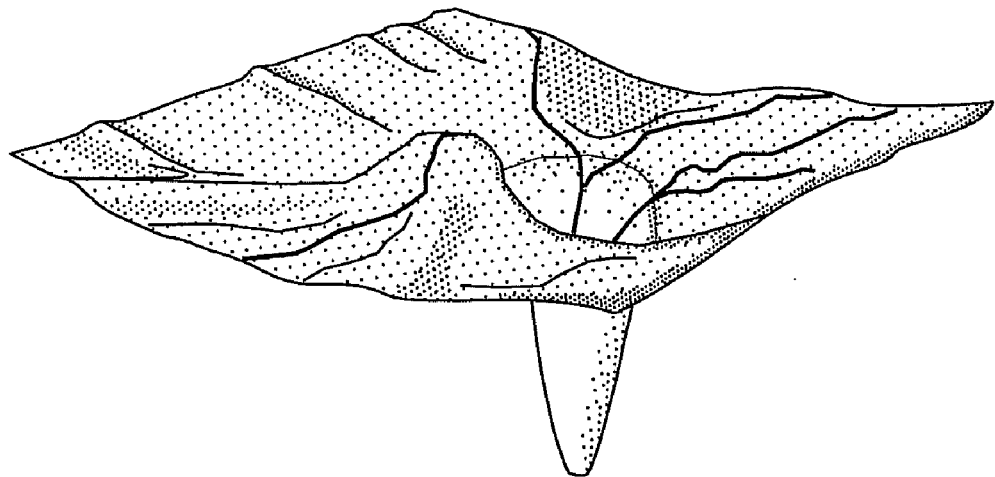
FIG. 7(a) shows a 3-D perspective image of a fundus image mapped to a surface topographical map of a retina.
Figure 7B:
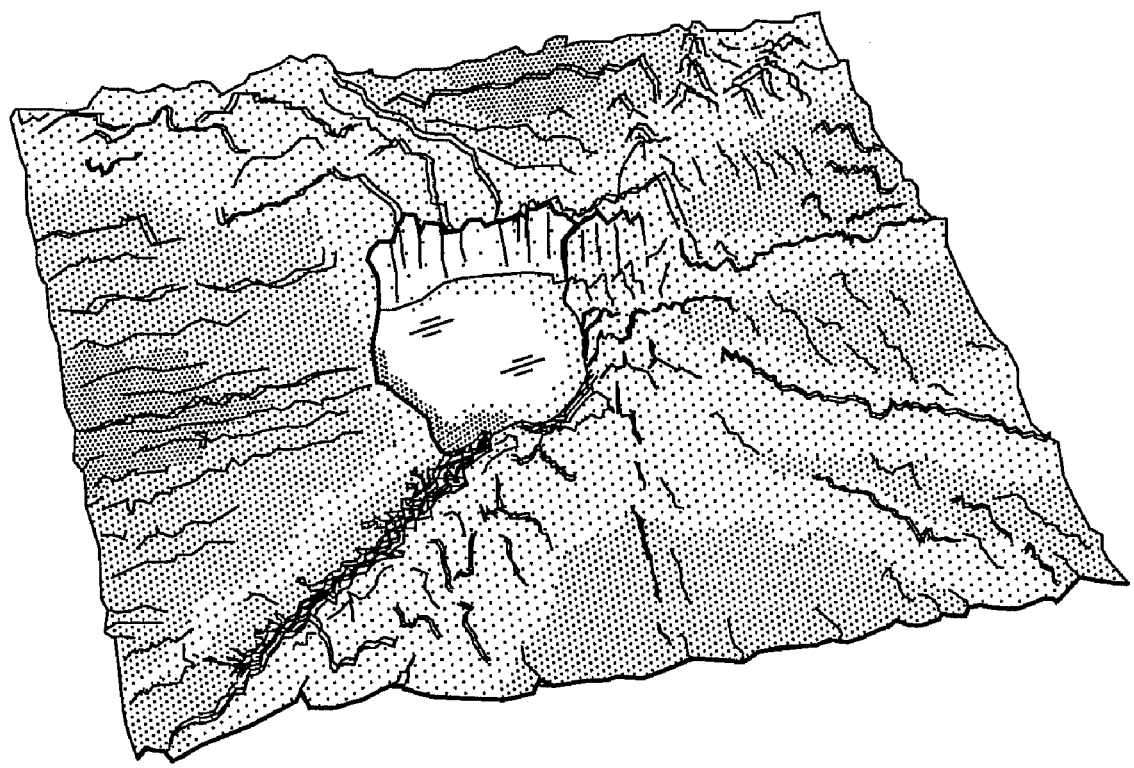
FIG. 7(b) is a 3-D perspective image of a fundus image mapped to a retinal thickness topograph.

Herein, a retinal characterization dataset refers to a retinal parameter dataset or to a fundus image. Herein, a composite retinal map refers to a graphical map of a second retinal characterization dataset mapped to a graphical map of a first characterization dataset. For example, a composite retinal map may refer to a graphical map of a second retinal parameter dataset (such as retinal thickness) mapped to a graphical map of a first retinal parameter dataset (such as surface topography). A composite retinal map may also refer to a fundus image mapped to a graphical map of a retinal parameter dataset, and to a graphical map of a retinal dataset mapped to a fundus image. FIG. 7(a), for example, shows a 3-D perspective image of a fundus image mapped to a surface topographical map of a retina. FIG. 7(b), for example, shows a 3-D perspective image of a fundus image mapped to a retinal layer thickness topograph. A composite retinal map may also include graphical maps of more than two retinal characterization datasets.

In an embodiment, a first retinal characterization dataset is convolved with a second retinal characterization dataset according to user-defined schemes and criteria. The convolved datasets are rendered into 2-D images, which are displayed on a monitor. Different views may be rendered, for example, 2-D cross-section, 2-D composite, and 3-D perspective. The images may be interactively manipulated by a user. For example, the user may click on an image with a mouse to change various parameters such as scale, field of view, orientation, perspective, contrast, false color, interface delineation, warp, and morph.

Figure 8:
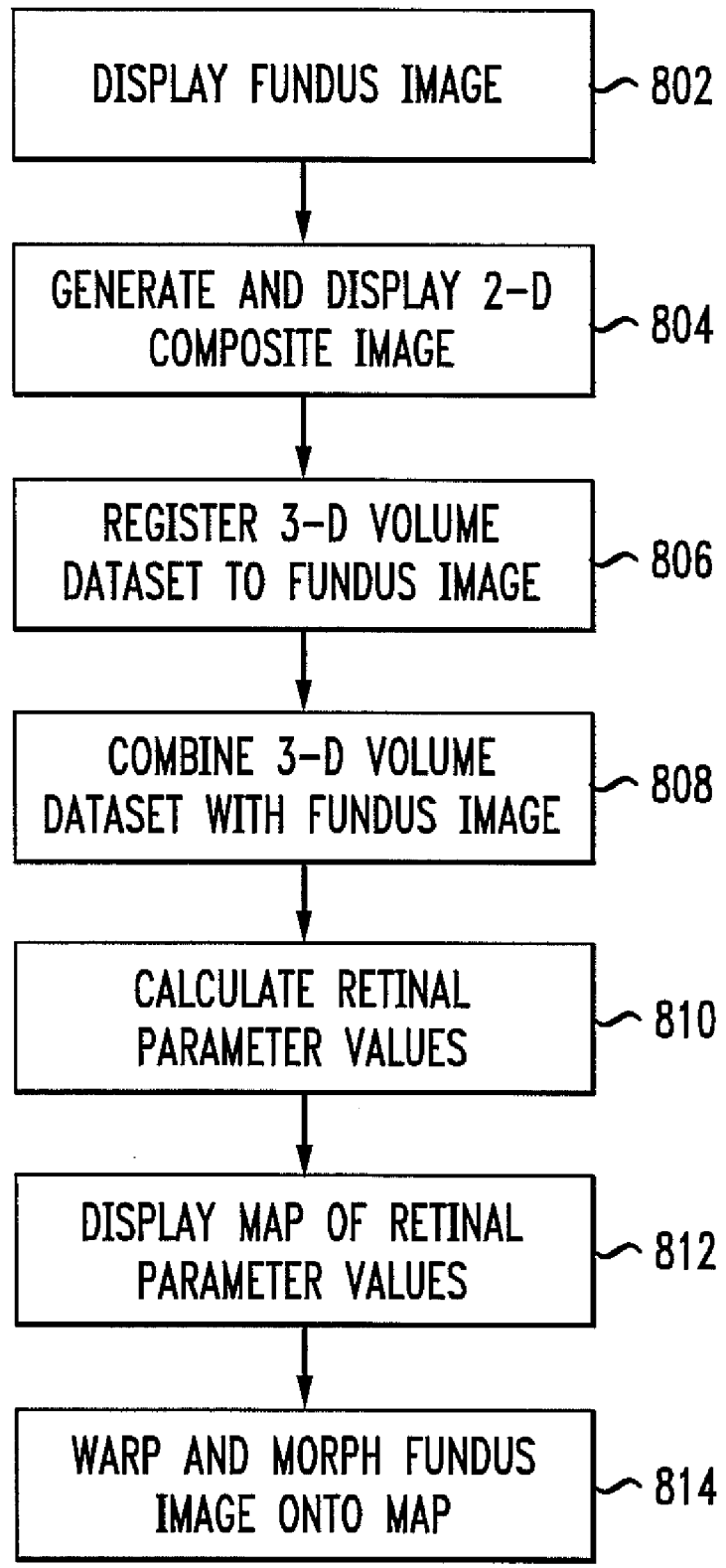
FIG. 8 shows a flowchart of steps for mapping a fundus image to a retinal parameter map.

FIG. 8 shows a flowchart which summarizes steps for mapping a fundus image onto a retinal layer thickness map. In step 802, a fundus image [such as Fundus Image 404F in FIG. 4(a)], is displayed on a monitor. The process then passes to step 804, in which a 2-D composite image [such as 2-D Composite Image 420C in FIG. 4(b)] is generated from a 3-D OCT volume dataset and displayed on the same monitor. The process then passes to step 806, in which the 3-D OCT volume dataset is registered to the fundus image by superimposing characteristic features in the 2-D composite image onto corresponding characteristic features in the fundus image. For example, referring back to FIG. 4(b), 2-D Composite Image 420C is moved until the set of characteristic features (Fovea 406C, Lesion 408C, and Blood Vessel 410C) in 2-D Composite Image 420C is superimposed onto the corresponding set of characteristic features (Fovea 406F, Lesion 408F, and Blood Vessel 410F) in Fundus Image 404F.

In step 808, a retinal parameter dataset (for example, retinal layer thickness in FIG. 6(b)) is calculated from the 3-D OCT volume dataset. The process then passes to step 810, in which a graphical map of the retinal layer thickness is displayed on the monitor. The process then passes to step 814, in which the fundus image is warped and morphed onto the graphical map of the retinal layer thickness, as shown in FIG. 7(b), for example.

One embodiment of a measurement and image processing system for mapping one retinal characterization dataset to another retinal characterization dataset may be implemented by using a computer. For example, the steps shown in the flowchart in FIG. 8 may be performed with a computer. As shown in FIG. 9, computer 902 may be any type of well-known computer comprising a central processing unit (CPU) 904, memory 908, data storage 906, and user input/output interface 910. Data storage 906 may comprise a hard drive or non-volatile memory. User input/output interface 910 may comprise a connection to a user input device 920, such as a keyboard or mouse. As is well known, a computer operates under control of computer software which defines the overall operation of the computer and applications. CPU 904 controls the overall operation of the computer and applications by executing computer program instructions which define the overall operation and applications. The computer program instructions may be stored in data storage 906, or other computer readable media, and loaded into memory 908 when execution of the program instructions is desired.

Computer 902 may further comprise a video display interface 916, which may transform signals from CPU 904 to signals which may drive video display 926. Computer 902 may further comprise one or more network interfaces. For example, communications network interface 918 may comprise a connection to an Internet Protocol (IP) communications network 928, which may transport test data or user data and commands.

Computer 902 may further comprise fundus image data interface 912 which may provide communication between computer 902 and fundus image data source 922, which may, for example, be a digital fundus camera. Computer 902 may further comprise 3-D OCT data interface 914, which may, for example, provide communication between computer 902 and 3-D OCT data source 924, which may, for example, be a 3-D OCT ophthalmic diagnostic instrument. In an embodiment, fundus image data source 922 and 3-D OCT data source 924 may be databases which may be transferred to data storage 906 via fundus image data interface 912 and 3-D OCT data interface 914. Databases may also be transferred to data storage 906 via communications network 928 and communications network interface 918. Computers are well known in the art and will not be described in detail herein.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for mapping a second retinal characterization dataset to a first retinal characterization dataset, comprising the steps of:
   displaying on a display a first graphical map based at least in part on the first retinal characterization dataset, wherein the first graphical map corresponds to a retinal region;
   generating a second graphical map based at least in part on the first graphical map and on the second retinal characterization dataset; and warping and morphing said second graphical map onto said first graphical map, wherein said second graphical map, after warping and morphing, corresponds to said retinal region.

2. The method of claim 1, wherein
said first retinal characterization dataset is a fundus image; and
said second retinal characterization dataset is a retinal parameter dataset.

3. The method of claim 2, wherein
said retinal parameter dataset is calculated from a three-dimensional optical coherence tomography (3-D OCT) volume dataset registered to said fundus image.

4. The method of claim 2, wherein said retinal parameter dataset characterizes at least one of:
retinal thickness; and
retinal layer thickness.

5. The method of claim 1, wherein
said first retinal characterization dataset is a retinal parameter dataset; and
said second retinal characterization dataset is a fundus image.

6. The method of claim 5, wherein
said retinal parameter dataset is calculated from a 3-D OCT volume dataset registered to said fundus image.

7. The method of claim 5, wherein said retinal parameter dataset characterizes at least one of:
retinal thickness;
retinal layer thickness; and
surface topography.

8. The method of claim 1, wherein
said first retinal characterization dataset is a first retinal parameter dataset; and
said second retinal characterization dataset is a second retinal parameter dataset.

9. The method of claim 8, wherein:
said first retinal parameter dataset and said second retinal parameter dataset are calculated from a 3-D OCT volume dataset registered to a fundus image.

10. The method of claim 8, wherein said first retinal parameter dataset and said second retinal parameter dataset characterize at least one of:
retinal thickness; and
retinal layer thickness.

11. An apparatus for mapping a second retinal characterization dataset to a first retinal characterization dataset, comprising:
means for displaying a first graphical map based at least in part on the first retinal characterization dataset, wherein the first graphical map corresponds to a retinal region;
means for generating a second graphical map based at least in part on the first graphical map and on the second retinal characterization dataset; and
means for warping and morphing said second graphical map onto said first graphical map, wherein said second graphical map, after warping and morphing, corresponds to said retinal region.

12. The apparatus of claim 11, wherein
said first retinal characterization dataset is a fundus image; and
said second retinal characterization dataset is a retinal parameter dataset.

13. The apparatus of claim 12, wherein
said retinal parameter dataset is calculated from a three-dimensional optical coherence tomography (3-D OCT) volume dataset registered to said fundus image.

14. The apparatus of claim 12, wherein said retinal parameter dataset characterizes at least one of:
retinal thickness; and
retinal layer thickness.

15. The apparatus of claim 11, wherein
said first retinal characterization dataset is a retinal parameter dataset; and
said second retinal characterization dataset is a fundus image.

16. The apparatus of claim 15, wherein
said retinal parameter dataset is calculated from a 3-D OCT volume dataset registered to said fundus image.

17. The apparatus of claim 15, wherein said retinal parameter dataset characterizes at least one of:
retinal thickness;
retinal layer thickness; and
surface topography.

18. The apparatus of claim 11, wherein
said first retinal characterization dataset is a first retinal parameter dataset; and
said second retinal characterization dataset is a second retinal parameter dataset.

19. The apparatus of claim 18, wherein:
said first retinal parameter dataset and said second retinal parameter dataset are calculated from a 3-D OCT volume dataset registered to a fundus image.

20. The apparatus of claim 18, wherein said first retinal parameter dataset and said second retinal parameter dataset characterize at least one of:
retinal thickness; and
retinal layer thickness.

21. A non-transitory computer readable medium storing computer instructions for mapping a second retinal characterization dataset to a first retinal characterization dataset, the computer instructions defining the steps of:
displaying on a display a first graphical map based at least in part on the first retinal characterization dataset, wherein the first graphical map corresponds to a retinal region;
generating a second graphical map based at least in part on the first graphical map and on the second retinal characterization dataset; and
warping and morphing said second graphical map onto said first graphical map, wherein said second graphical map, after warping and morphing, corresponds to said retinal region.

22. The non-transitory computer readable medium of claim 21, wherein
said first retinal characterization dataset is a fundus image; and
said second retinal characterization dataset is a retinal parameter dataset.

23. The non-transitory computer readable medium of claim 22, wherein
said retinal parameter dataset is calculated from a three-dimensional optical coherence tomography (3-D OCT) volume dataset registered to said fundus image.

24. The non-transitory computer readable medium of claim 22, wherein said retinal parameter dataset characterizes at least one of:
retinal thickness; and
retinal layer thickness.

25. The non-transitory computer readable medium of claim 21, wherein
said first retinal characterization dataset is a retinal parameter dataset; and
said second retinal characterization dataset is a fundus image.

26. The non-transitory computer readable medium of claim 25, wherein
said retinal parameter dataset is calculated from a 3-D OCT volume dataset registered to said fundus image.

27. The non-transitory computer readable medium of claim 25, wherein said retinal parameter dataset characterizes at least one of:
retinal thickness;
retinal layer thickness; and
surface topography.

28. The non-transitory computer readable medium of claim 21, wherein
said first retinal characterization dataset is a first retinal parameter dataset; and
said second retinal characterization dataset is a second retinal parameter dataset.

29. The non-transitory computer readable medium of claim 28, wherein:
said first retinal parameter dataset and said second retinal parameter dataset are calculated from a 3-D OCT volume dataset registered to a fundus image.

30. The non-transitory computer readable medium of claim 28, wherein said first retinal parameter dataset and said second retinal parameter dataset characterize at least one of:
retinal thickness; and
retinal layer thickness.

* * * * *